(12) United States Patent
St. George-Hyslop et al.

(10) Patent No.: US 6,955,896 B2
(45) Date of Patent: Oct. 18, 2005

(54) ALZHEIMER'S RELATED PROTEINS AND METHODS OF USE

(75) Inventors: Peter H. St. George-Hyslop, Toronto (CA); Paul E. Fraser, Toronto (CA)

(73) Assignee: The Governing Council of the Unversity of Toronto, Ontario (CA)

( * ) Notice: Subject to any disclaimer, the term of this patent is extended or adjusted under 35 U.S.C. 154(b) by 305 days.

(21) Appl. No.: 10/071,900

(22) Filed: Feb. 8, 2002

(65) Prior Publication Data

US 2002/0127541 A1 Sep. 12, 2002

Related U.S. Application Data

(62) Division of application No. 09/227,725, filed on Jan. 8, 1999, now Pat. No. 6,383,758
(60) Provisional application No. 60/070,948, filed on Jan. 9, 1998.

(51) Int. Cl.[7] ........................... C12P 21/06; G01N 33/53
(52) U.S. Cl. ........................................ 435/69.1; 435/7.1
(58) Field of Search ................................ 435/69.1, 7.1

(56) References Cited

U.S. PATENT DOCUMENTS

| | | | |
|---|---|---|---|
| 5,449,604 A | 9/1995 | Schellenberg et al. | 435/6 |
| 5,840,540 A | 11/1998 | St. George-Hyslop et al. | 435/69.1 |
| 6,020,143 A | 2/2000 | St. George-Hyslop | 435/7.1 |

FOREIGN PATENT DOCUMENTS

| | | | |
|---|---|---|---|
| EP | 341 491 A2 | 11/1989 | C12Q/1/68 |
| WO | WO 92/17152 | 10/1992 | |
| WO | WO 95/05466 | 2/1995 | C12N/15/54 |
| WO | WO 96/30499 | 10/1996 | C12N/15/12 |
| WO | WO 97/03192 | 1/1997 | C12N/15/12 |
| WO | WO 97/27296 | 7/1997 | C12N/15/12 |
| WO | WO 98/01549 | 1/1998 | C12N/15/12 |

OTHER PUBLICATIONS

Levitan et al., Nature 377:351–354, 1995.
Levy–Lahad et al., Science 269:970–973, 1995.
Levy–Lehad et al., Science 269:973–977, 1995.
Li et al., Proc. Natl. Acad. Sci 92:12180–12184, 1995.
Rogaev et al., Nature 376:775–778, 1995.
Schellenberg et al., Science 258:678–671, 1992.
Sherrington et al., Nature 375:754–760, 1995.
Wasco et al., Nature Medicine 1(9):848, 1995.
Zhou et al., Neuroreport 8:2085–2090, 1997.

*Primary Examiner*—Karen Cochrane Carlson
(74) *Attorney, Agent, or Firm*—Darby & Darby

(57) ABSTRACT

Disclosed is a method for identifying substances that alter the interaction of a presenilin protein with a presenilin-binding protein, including contacting at least the interacting domain of a presenilin protein to a presenilin-binding protein in the presence of a test substance, and measuring the interaction of the presenilin protein and the presenilin-binding protein. Also disclosed is method for identifying substances that modulate the nuclear translocation of an armadillo protein, including providing a culture of cells that express the armadillo protein and a mutant presenilin protein, or a functional fragment thereof that binds an armadillo protein; contacting the culture with a test substance; inducing nuclear translocation of the armadillo protein in the cells; and measuring levels of nuclear armadillo protein as compared to a control as an indication of modulatory activity of the test substance. Further disclosed is method for screening individuals for presenilin alleles associated with Alzheimer's Disease or related disorders, including obtaining cells from an individual to be tested for Alzheimer's Disease or a related disorder; inducing nuclear translocation of an armadillo protein in the cells; and measuring levels of the nuclear armadillo protein as compared to a control as an indication of the presence or absence of presenilin alleles associated with Alzheimer's Disease or a related disorder.

16 Claims, 3 Drawing Sheets

```
  1    MP.A.PEQASLVEEGQPQTRQEAASTGPCMEPLTTATTILASVK.EQELQF....
  1    MTFNAGP———SLL——SQ————S——ALQ————LNS—KPEGSPQYPASY

89    PWRSTDVPNTGVSKP.RV..SD.A..VQPNNYLIRTEPEQGTLYSPEQTSLHESEG
 62    S.QCT..T..SRAGHLACPEPAPPPPPP.....R.EP......EAP...SL....G

174    NRQQHSFIGS.TNNHVVR.NSRA.EGQTLVQPSVANRAMRRVSSVPSRAQSPSYVI
131    ..PQ.C..GSPTK..LQRCCS.APECATY......A..A.PRGSS.P.K.QSPS..

270    RAASPYSQRPASPTAIRRIGSVTSRQTSNPNGPTPQYQTTARVGSPLTLTDAQTRV
186    ........SP..IR.....VTS......P..PTV.QST.ISS..

366    QYDIY..ERMVPPRPDSL.TCLRSSYASQHSQLGQDLRSAV.SPDLHITPIYECRT
236    Q.ELYATATL..QRPCSLAAGSRASYSSQHGHLCPELR.ALQSPEHHIDPIYEDRV
```

FIG. 1A

```
453  LQRTSSQRS......TLTYQRNNYALNTTAT YAEPYRPIQY..RVQECNYNRLQHA
328  LQRTCSQHGPQNAAAATFQRASYA.AGPASNYADPYRQLQYCPSV ESPYSKSCPA.

544  VQANAAAYLQHLCFGDNKVKMEVCRLCGIKH LVDLLDHRVL.EVQKNACGALRNL
425  VQSNAAAYLQHLCPCDNKIKAFIRRQGGI.QLLVDLLDHR.MTEVHRSACGALRNL
     |<<<<Arm Repeat 1>>>>>|              |<<<<<<Arm Rep 642  LSSCDAVKMTIIRDALSTLTNTVIVPHSCWNNSSFDDDHKIKFQTSLVLRNTTGCL
523  LSSCDALKMPIIQDALAVLTNAVIIPHSGWENSPLQDDRKIQLHSSQVLRNATGCL
     <Arm Repeat 3>>>|                    |<<<<<<<<Arm 742  CVCTLRNLSYRLELEVPQARLLGLNELDDLL GKESPSKDSEPS.CWGKKKKKKR
623  CVCILRNLSYRLAAETSQCQHMCTDELDGLLCG.EANGKDAESSCCWGKKKKKK.
     |<<<<<<<<Arm Repeat 5>>|              |<<<<<Arm Repeat 6>>>>>>>>|
```

FIG. 1B

```
839  NPATLECSACSLQNLSA.SNWKFAAYIRGG.RPKRKCLPILVELLRMDNDRVVSSC
718  NPDTLECAAGALQNLAAGS WKWSVYIRAAVR.KEKGLPILVELLRIDNDRVVCAV
     <<<<<<Arm Repeat 7>>>>>>>>       <<<<<<<<<<<

932  DETMAAICCALHEV.TSKNMENAKALADSGGIEKLVNITKGRGDR.SSLKVVKAAA
816  DDTVTAVCCTLHEVIT KNMENAKALRDAGGIEKLVCISKSKGDKHSP.KVVKAAS
     <<<<<<Arm Repeat 9>>>>>>>>       |<<<<<<<<<<Ar 1027 PSLS.TTNQQMSPI IQSVG..STS..SSP ALLGIRDPRSEYDRT. QPPMQYYN
912  .S.SRTPS..ISPVRV SPNNRSASAPASPREMISLKERKTDYECTGSNAT..YHG 1115 YYS.Q...DD.SNRKNFDAYRLYLQ.SPHSYEDPYEDDRVHF..PASTDYST.QYG
1000 ..SAQPVPQEPS.RKDYETYQPP.QNSTRNYDESFFEDQVHHRPPAS EY TMHLC
```

FIG. 1C

ALZHEIMER'S RELATED PROTEINS AND METHODS OF USE

CROSS REFERENCE TO RELATED APPLICATION

This application is a divisional of U.S. Ser. No. 09/227,725, filed Jan. 8, 1999, issued as U.S. Pat. No. 6,383,758, May 7, 2002, which claims the benefit of U.S. Provisional Application No. 60/070,948, filed Jan. 9, 1998. Each of these prior applications is hereby incorporated by reference in its entirety.

FIELD OF THE INVENTION

The present invention relates generally to the field of neurological and physiological dysfunctions associated with Alzheimer's Disease. More particularly, the invention is concerned with the identification of proteins associated with Alzheimer's Disease, to methods of diagnosing Alzheimer's Disease and to methods of screening for candidate compounds which modulate the interaction of certain proteins, specifically armadillo repeat proteins, with presenilin proteins.

BACKGROUND OF THE INVENTION

Alzheimer's Disease (AD) is a degenerative disorder of the human central nervous system characterized by progressive memory impairment and cognitive and intellectual decline during mid to late adult life (Katzman, 1986, *N. Eng. J. Med.* 314:964–973). The disease is accompanied by a constellation of neuropathologic features principal amongst which are the presence of extracellular amyloid or senile plaques, and neurofibrillary tangles in neurons. The etiology of this disease is complex, although in some families it appears to be inherited as an autosomal dominant trait. Genetic studies have identified three genes associated with the development of AD, namely: (1) β-amyloid precursor protein (βAPP) (Chartier-Harlin et al., 1991, *Nature* 353:844–846; Goate et al., 1991, *Nature* 349:704–706; Murrell et al., 1991, *Science* 254:97–99; Karlinsky et al., 1992, *Neurology* 42:1445–1453; Mullan et al., 1992, *Nature Genetics* 1:345–347); (2) presenilin-1 (PS1) (Sherrington et al., 1995, *Nature* 375:754–760); and (3) presenilin-2 (PS2) (Rogaev et al., 1995, *Nature* 376:775–778; Levy-Lehad et al., 1995, *Science* 269:970–973).

The presenilin genes (presenilin 1—PS1 and presenilin 2—PS2) encode homologous polytopic transmembrane proteins that are expressed at low levels in intracellular membranes including the nuclear envelope, the endoplasmic reticulum, the Golgi apparatus and some as yet uncharacterised intracytoplasmic vesicles in many different cell types including neuronal and non-neuronal cells (Sherrington et al., 1995; Rogaev et al., 1995; Levy-Lahad et al., 1995; Doan et al., 1996, *Neuron* 17:1023–1030; Walter et al., 1996, *Molec. Medicine* 2:673–691; De Strooper et al., 1997, *J. Biol. Chem* 272:3590–3598; Lehmann et al., 1997, *J.Biol.Chem.* 272:12047–12051; Li et al., 1997, *Cell* 90:917–927). Structural studies predict that the presenilins contain between six and eight transmembrane (TM) domains organized such that the N-terminus, the C-terminus, and a large hydrophilic loop following the sixth TM domain are located in the cytoplasm or nucleoplasm, while the hydrophilic loop between TM1 and TM2 is located within the lumen of membranous intracellular organelles (Doan et al., 1996; De Strooper et al., 1997; Lehmann et al., 1997).

Missense mutations in the PS1 and PS2 genes are associated with the inherited forms of early-onset AD (Sherrington et al., 1995, *Nature* 375:754–760; Rogaev, et al., 1995, *Nature* 376:775–778; Levy-Lahad et al, 1995, *Science* 269: 970–973). Several lines of evidence have also suggested roles in developmental, apoptotic signalling and in the regulation of proteolytic cleavage of the b-amyloid precursor protein (bAPP) (Levitan et al., 1995, *Nature* 377:351–354; Wong et al., 1997, *Nature* 387:288–292; Shen et al., 1997, *Cell* 89:629–639; Wolozin et al., 1996, *Science* 274:1710–1713; De Strooper et al., 1998, *Nature* 391:387–390). Nevertheless, it remains unclear just how these putative functions are mediated, or how they relate to the abnormal metabolism of the βAPP associated with PS1 and PS2 mutations (Martin et al., 1995, *NeuroReport* 7:217–220; Scheuner et al., 1996, *Nature Med.* 2:864–870; Citron et al., 1997, *Nature Med.* 3:67–72; Duff et al., 1996, *Nature* 383:710–713; Borchelt et al., 1996, *Neuron* 17:1005–1013).

The identification and cloning of normal as well as mutant PS1 and PS2 genes and gene products are described in detail in copending commonly assigned U.S. application Ser. No. 08/431,048, filed Apr. 28, 1995; Ser. No. 08/496,841, filed Jun. 28, 1995; Ser. No. 08/509,359, filed Jul. 31, 1995; and Ser. No. 08/592,541, filed Jan. 26, 1996, the disclosures of which are incorporated herein by reference.

There is speculation that onset of AD may be associated with aberrant interactions between mutant presenilin proteins and normal forms of PS-interacting proteins, and these changes may increase or decrease interactions present with normal PS1, or cause interaction with a mutation-specific PS-interacting protein. Such aberrant interactions also may result from normal presenilins binding to mutant forms of the PS-interacting proteins. Therefore, mutations in the PS-interacting proteins may also be causative of AD.

While the identification of normal and mutant forms of PS proteins has greatly facilitated development of diagnostics and therapeutics, a need exists for new methods and reagents to more accurately and effectively diagnose and treat AD.

SUMMARY OF THE INVENTION

Applicants have discovered that both PS1 and PS2 interact specifically with at least two members of the armadillo family of proteins (GT24/Neuronal Plakoglobin Related Armadillo Protein and β-catenin) that are expressed in both embryonic and post-natal tissues. Moreover, the domains of PS1 and PS2 that interact with these proteins have been identified. Applicants have also discovered that mutations in PS1 and PS2 affect the translocation of β-catenin into the nucleus of both native cells and cells transfected with a mutant PS gene. These discoveries provide the basis for materials and methods useful in the diagnosis and treatment of AD.

One object of the invention is directed to a method for identifying substances that alter the interaction of a presenilin protein with a presenilin-binding protein, comprising:

(a) contacting at least the interacting domain of a presenilin protein to a presenilin-binding protein in the presence of a test substance, and (b) measuring the interaction of the presenilin protein and the presenilin-binding protein. Preferably, the interacting domain is contained in or contains the sequence of amino acid residues from about 260 to about 409 of a mutant PS1 protein, more preferably the sequence of amino acid residues from about 372 to about 399, in which the amino acid positions correspond to the wild-type human PS1 sequence defined by SEQ ID NO:1. When PS2 is used, the sequence of amino acid residues from about 266 to about 390 are preferred, more preferably the sequence of amino residues from about 350 to about 380, in which the amino acid positions correspond to the wild-type human PS2 sequence defined by SEQ ID NO:2.

Substances identified that alter the interaction of a mutant presenilin protein with a normal presenilin-interacting protein, as well as the interaction of a normal presenilin protein with a mutant presenilin-interacting protein, are putative candidates for use in the diagnosis and treatment of AD.

Another object of the invention is to provide methods of identifying substances that modulate the nuclear translocation of an armadillo protein, comprising:

(a) providing a culture of cells that express the armadillo protein and a mutant presenilin protein, or a functional fragment thereof that binds said armadillo protein;

(b) contacting said culture with a test substance;

(c) inducing nuclear translocation of said armadillo protein in said cells; and (d) measuring levels of nuclear armadillo protein as compared to a control as an indication of modulatory activity of said test substance. Alternatively, step (d) may comprise the step of measuring the effects of altered nuclear translocation such as: (i) alterations in transcription of downstream genes such as βAPP, γ-secretase, or by alteration in the activity of a transcription reporter assay such as the Tcf/Lef-luciferase assay; (ii) alterations in cellular responsiveness to signalling molecules (e.g., Wnt, EGF) which use armadillo proteins for intracellular signal transduction; or (iii) alterations in cell:cell adhesion (e.g., synapse formation) mediated by cytoplasmic armadillo proteins.

Armadillo proteins of the present invention include, but are not limited to, hNPRAP, p0071 and β-catenin. Cells may be native or recombinant (i.e., the mutant PS gene and/or the armadillo protein gene are/is transgenic to the cell).

It is another object of the invention to provide methods for screening for carriers of presenilin alleles associated with AD or related disorders, comprising:

(a) obtaining cells from an individual to be tested for Alzheimer's Disease or a related disorder;

(b) culturing said cells with a substance which induces nuclear translocation of an armadillo protein; and (c) measuring levels of nuclear armadillo protein as compared to a control as an indication of the presence or absence of presenilin alleles associated with Alzheimer's Disease or a related disorder. Alternatively, step (c) may comprise measuring effects of altered nuclear translocation such as: (i) alterations in transcription of downstream genes such as βAPP, γ-secretase, or by alteration in the activity of a transcription reporter assay such as the Tcf/Lef-luciferase assay; (ii) alterations in cellular responsiveness to signalling molecules (e.g., Wnt, EGF) which use armadillo proteins for intracellular signal transduction; or (iii) alteration in cell:cell adhesion (e.g., synapse formation) mediated by cytoplasmic armadillo proteins.

Inducement of nuclear translocation of the armadillo protein is preferably performed by activating the Wnt/armadillo signal transduction pathway of the cells. Most preferably, activation is with a lithium salt (e.g., lithium chloride) or with methods such as with recombinant Wnt proteins (or invertebrate homologues, e.g., Wingless proteins) applied exogenously to the medium or via transfection into the test cells.

BRIEF DESCRIPTION OF THE FIGURES

FIGS. 1A–1C show the amino acid sequences of GT24/hNPRAP and p0071 and the location of the 10 armadillo repeats.

DETAILED DESCRIPTION OF THE INVENTION

Applicants have identified the presenilin domain i.e., the interacting domain, that interacts with PS-interacting proteins, such as armadillo repeat proteins hNPRAP, p0071 and β-catenin, as including or contained in the sequence of amino acid residues from about 260 to about 409 of PS1 or corresponding residues from about 260 to about 390 in PS2. More preferably, the interacting domain contains or is contained in amino acid residues from about 372 to about 399 of PS1 or corresponding residues from about 350 to about 380 in PS2. The amino acid sequences of wild-type human PS1 and PS2 are shown in SEQ ID NO:1 and SEQ ID NO:2, respectively.

Mutant PS1 and PS2 genes, and their corresponding amino acid sequences are described in Applicants' co-pending U.S. application Ser. No. 08/888,077, filed Jul. 3, 1997, and incorporated herein by reference. Examples of PS1 mutants include I143T, M146L, L171P, F177S, A260V, C263R, P264L, P267S, E280A, E280G, A285V, L286V, Δ291–319, L322V, G384A, L392V, C410Y and I439V. The mutations are listed with reference to their amino acid positions in SEQ ID NO:1. Examples of PS2 mutants include N141I, M239V and I420T. These mutations are listed with reference to their amino acid positions in SEQ ID NO:2. PS1 mutations A260V, C263R, P264L, P267S, E280A, E280G, A285V, L286V, Δ291–319, G384A, L392V, and C410Y all occur in or near the interacting domain of PS1 described herein. However, the methods of the present invention are not limited to mutant presenilins wherein the interacting domain is mutated relative to the wild-type protein. For example, Applicants have observed that mutations in PS1 (e.g., M146L) which are not in the interacting domain (loop) also affect β-catenin translocation. These mutations probably disturb the presenilin armadillo interactions by altering the function of a high MW complex which contains the presenilin and armadillo proteins (plus others), as described in Yu et al., 1998, *J.Biol.Chem.* 273:16460–16475; Levesque et al., 1999, *J. Neurochem.*, in press; and Nishimura et al., 1999, *Nature Medicine*, in press. Moreover, a comparison of the hPS1 and hPS2 sequences reveals that these pathogenic mutations are in regions of the PS1 protein which are conserved in the PS2 protein. Therefore, corresponding mutations in corresponding regions of PS2 may also be expected to be pathogenic and are useful in the methods described herein.

Proteins that interact with the presenilins, i.e., PS-interacting proteins, include the S5a subunit of the 26S proteasome (GenBank Accession No. 451007), Rab11 (GenBank Accession Nos. X5670 and X53143), retinoid X receptor B, also known as nuclear receptor co-regulator or MHC (GenBank Accession Nos. M84820, X63522 and M87166) and GT24 (GenBank Accession No. U81004). These and other PS1 binding proteins such as armadillo proteins are described in Applicants' copending commonly assigned U.S. application Ser. No. 08/888,077, filed Jul. 3, 1997, as well as U.S. application Ser. No. 08/592,541, filed Jan. 26, 1996, the disclosures of which are incorporated herein by reference. The interaction between PS1 and β-catenin is reported by Zhou et al., 1997, *Neuro. Report (Fast Track)* 8:1025–1029 and Yu et al., 1998; Levesque et al, 1999; and Nishimura et al., 1999. Mutant forms as well as wild-type presenilin-interacting proteins may be used in the methods described herein. By presenilin-interacting proteins it is meant full-length proteins or fragments that contain the domain that interacts with the presenilin-interacting domain of a presenilin protein.

A first embodiment is directed to a method for identifying substances that alter the interaction of a presenilin protein with a presenilin-binding protein or which alter the functional consequences of the interaction. Candidate compounds which are shown to modulate these interactions may be produced in pharmaceutically useful quantities for use in the diagnosis and treatment of AD or related disorders. Candidate compounds include endogenous cellular components which interact with the presenilins in vivo and which, therefore, provide new targets for pharmaceutical and therapeutic interventions, as well as recombinant, synthetic and otherwise exogenous compounds which may have presenilin binding capacity and, therefore, may be candidates for pharmaceutical agents. Thus, in one procedure, cell lysates or tissue homogenates (e.g., human brain homogenates, lymphocyte lysates) may be screened for proteins or other compounds which bind to one of the normal or mutant presenilins. Alternatively, any of a variety of exogenous compounds, both naturally occurring and/or synthetic (e.g., libraries of small molecules or peptides), may be screened for presenilin binding capacity. In each of these embodiments, an assay is conducted to detect binding between a presenilin component containing at least the interacting domain of a presenilin protein described herein and some other moiety. Binding may be detected by indirect functional measures reflecting the functional consequences of the interaction (e.g., changes in intracellular $Ca^{2+}$, $Na^+$, $K^+$, or GTP/GDP ratio, changes in apoptosis or microtubule associated protein phosphorylation, changes in Aβ peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of presenilin components and bound proteins or other compounds by immunoprecipitation; (3) BIAcore analysis; and (4) the yeast two-hybrid systems. Other procedures include methods which detect abnormal processing of PS1, PS2, APP, or proteins reacting with PS1, PS2, or APP (e.g., abnormal phosphorylation, glycosylation, glycation amidation or proteolytic cleavage) alterations in presenilin transcription, translation, and post-translational modification; alterations in the intracellular and extracellular trafficking of presenilin gene products; or abnormal intracellular localization of the presenilins.

A second embodiment is directed to a method for identifying substances that modulate the nuclear translocation of armadillo proteins, preferably β-catenin, hNPRAP (GT24) and p0071. Nuclear translocation assays can advantageously be used as a biological monitor of the effects of PS1 and PS2 mutations that cause AD. This interaction can be modulated by compounds which strengthen or weaken the interaction between PS1 and PS2 and armadillo repeat proteins. This interaction assay method finds use in both the diagnosis and treatment of AD.

Generally, paired cell lines (e.g., vertebrate cells, such as the ones used in the Examples described herein or invertebrate cells, such as *D. melanogaster* cells) may be used in the method. One set of cells (control), expresses wild-type PS1 and wild-type armadillo protein (e.g., hNPRAP, p0071, β-catenin). The second set of cells expresses mutant PS1 and wild-type armadillo protein (test). By the terms PS1 and PS2, it is meant full-length or functional fragments thereof (e.g., residues 260–409 of PS1) that bind a normal or mutant armadillo protein. By the term armadillo protein, it is meant full-length protein or functional fragments thereof (e.g., one or more armadillo repeats) that bind PS1 or PS2. For rapid in vitro assays, armadillo protein may be labelled with green-fluorescent protein (GFP) or blue fluorescence protein and transfected into the cells. PS1 or PS2 is preferably present in the form of a transgene, but cells in which PS1 and armadillo protein are endogenously expressed, such as patient fibroblasts or cultured neurons from transgenic mouse brain, may be used. All vertebrate cells express β-catenin, but not all armadillo proteins are expressed in all cell types. Thus, cells may be transformed with a transgene encoding the armadillo protein of choice. Armadillo proteins and their corresponding nucleotide and amino acid sequences are known in the art. The sequence of hNPRAP (GT24) is described in U.S. application Ser. No. 08/888,077, filed Jul. 3, 1997, and is incorporated herein by reference.

The cells are then exposed to a candidate substance to be tested plus an environment or agent that induces nuclear translocation of the armadillo protein. In a preferred embodiment, nuclear translocation is achieved by culturing the cells in the presence of a lithium salt such as lithium chloride, exogenous recombinant Wnt/Wingless protein, NGF, EGF, Aβ, kinase inhibitors (e.g., Herbanycin A, Genstein or Lavendustin A), or phosphatase inhibitors such as $Na^+$ Vanidate. These agents modulate the Wnt/armadillo signal transduction pathway in the cells. The last three named agents are less preferred than the first two agents (lithium and Wnt/Wingless) because they modulate phosphorylation of many proteins other than just β-catenin. In a most preferred embodiment, nuclear translocation is induced by contacting the culture with a lithium salt, preferably lithium chloride, or Wnt/Wingless.

Nuclear armadillo protein levels are preferably measured by direct visualization. Levels of nuclear armadillo protein in test cells versus controls cells are then compared to determine whether the test substance modulates the nuclear translocation of armadillo protein. In one preferred procedure, the cells are fixed and stained with anti-β-catenin antibodies (where β-catenin is the armadillo protein utilised). The amount of nuclear β-catenin is subsequently quantified by counting relative numbers of β-catenin (+) and β-catenin (−) nuclei, and/or by measuring the optic density of microscopic images of nuclei. In another procedure, cells containing GFP-tagged-β-catenin are directly visualised for translocation in living cells under UV light. Nuclear β-catenin levels may be quantified as above. An advantage of this procedure is that it allows the same cell to be investigated using different conditions, for example using different quantities of the same or different test substances (drugs). In a further procedure, nuclei are isolated by known methods as described herein, and nuclear β-catenin levels are quantitatively measured by densitometry of signal intensity on Western blots probed with anti-β-catenin antibodies. In yet another procedure, nuclei from cells containing GFP-tagged β-catenin are isolated. Nuclear GFP-β-catenin is then quantified by direct measurement of GFP fluorescence signal intensity. In an alternative embodiment, the effects of altered nuclear translocation may be measured, e.g., measuring: (i) alterations in transcription of downstream genes such as βAPP, γ-secretase, or by alteration in the activity of a transcription reporter assay such as theTcf/Lef-luciferase assay; (ii) alterations in cellular responsiveness to signalling molecules (e.g., Wnt, EGF) which use armadillo proteins for intracellular signal transduction; or (iii) alterations in cell: cell adhesion (e.g., synapse formation) mediated by cytoplasmic armadillo proteins. Such procedures are well known to those skilled in the art, as described in Korinek et al., 1998, *Mol.Cell.Biol.* 18:1248–56; Morin et al., 1997, *Science*, 275:1787–90; Korinek et al., 1997, *Science*, 275:1784–87; and Molenaar et al., 1996, *Cell*, 86:391–92. In each of these procedures, the control may be cells that express the normal presenilin and armadillo protein genes.

The interacting domain of the presenilins can be used, together with presenilin binding proteins, or fragments thereof that bind to the interacting domain of PS1 or PS2, to screen for substances that alter (e.g., facilitate, interfere, inhibit, prevent) binding of PS1 and/or PS2 to presenilin binding proteins or alter the functional consequences of binding (i.e., nuclear translocation of armadillo proteins, changes in βAPP metabolism, transcription or translation, or changes in Aβ secretion). Such agents are candidates for use in the diagnosis or treatment of AD. Candidate substances may be selected from peptides, oligosaccharides, lipids, small molecules, compounds (drugs) or derivatives of any of the foregoing, or other molecules. Substances to be used in the screening methods of the invention may be obtained e.g., from chemical or natural product libraries, including bacterial, fungal, plant and animal extracts. Substances can be tested in accordance with the invention for the ability to interfere with the binding of presenilin to a presenilin-binding protein. Such compounds may be found, for example, in natural product libraries, fermentation libraries (encompassing plants and microorganisms), combinatorial libraries, compound files, and synthetic compound libraries.

In yet another embodiment of the invention, a method is provided to screen for carriers of alleles associated with AD or related disorders, for diagnosis of victims of AD, and for screening and diagnosis of related presenilin and senile dementias, psychiatric diseases such as schizophrenia and depression, and neurological disease such as stroke and cerebral hemorrhage, associated with mutations in the PS1 or PS2 genes or presenilin binding proteins. Any eukaryotic cell may be used in the method. Control cells may be cells from a normal individual, i.e., absense of alleles associated with AD or related disorders. In preferred embodiments, fibroblasts, leukocytes or neuronal cells are used. The armadillo protein assayed depends upon the type of cells obtained from the subject. Induction of nuclear translocation and visualization of the armadillo protein are conducted as described above. In an alternative embodiment, the effects of altered nuclear translocation may be measured in the cells obtained from the subject, e.g., measuring: (i) alterations in transcription of downstream genes such as βAPP, γ-secretase, or by alteration in the activity of a transcription reporter assay such as the Tcf/Lef-luciferase assay; (ii) alterations in cellular responsiveness to signalling molecules (e.g., Wnt, EGF) which use armadillo proteins for intracellular signal transduction; or (iii) alterations in cell:cell adhesion (e.g., synapse formation) mediated by cytoplasmic armadillo proteins. Such procedures are well known to those skilled in the art, as described in Korinek et al., 1998; Morin et al., 1997; Korinek et al., 1997; and Molenaar et al., 1996.

In general, modifications of the sequences encoding the polypeptides described herein may be readily accomplished by standard techniques such as chemical syntheses and site-directed mutagenesis. See Gillman et al., 1979, *Gene* 8:81–97; Roberts et al., 1987, *Nature* 328:731–734; and *Innis* (ed.), 1990, *PCR Protocols: A Guide to Methods and Applications*, Academic Press, New York. Most modifications are evaluated by routine screening via an assay designed to select for the desired property.

These and other aspects of the invention are described in more detail by reference to the following examples.

EXAMPLE 1

To identify cDNAs encoding PS1-binding proteins, a yeast two hybrid library containing human adult brain cDNAs was screened using three overlapping "bait" cDNA sequences derived from the $PS1_{266-409}$ cytoplasmic loop. These bait sequences were: 1) a wild type PS1 TM6–TM7 loop ($PS1_{266-409}$); 2) a PS1 Exon 10 splice mutant, which construct corresponds to the FAD-linked Δ290–319 mutation ($PS1_{266-289/320-409}$); and 3) a construct corresponding to the physiologic 18 kDa C-terminal cleavage fragment ($PS1_{290-467}$) which, in a six transmembrane (TM) model of PS1 topology, would be entirely cytoplasmic (Lehmann et al., 1997, *J.Biol.Chem.* 272:12047–12051) but in an eight TM model would contain two additional TM domains (Doan et al., 1996, *Neuron* 17:1023–1030).

The bait sequences were ligated into pAS2-1 (Clontech), were shown to be free of autonomous β-gal activation, and were independently co-transformed into Y190 *S. cerevisiae* together with a human brain cDNA library in pACT2 vector (Clontech). Transformants were selected for His$^+$, β-gal$^+$ activity, and the "trapped" candidate PS1 interacting cDNAs were isolated, sequenced, and analysed by BLASTN database searches. Negative control cDNAs included human Lamin C. Quantitative β-gal assays were performed according to the Matchmaker II protocol (Clontech).

Six of the 42 His$^+$, βgal$^+$ clones trapped by the wild type $PS1_{266-409}$ bait, one of ten clones trapped by the mutant $PS1_{260-289/320-409}$ bait, and one of six clones trapped by the C-terminal $PS1_{290-467}$ bait represented overlapping clones derived from the same transcript, termed GT24. (GenBank Accession No. U81004.)

Nucleotides 2920–2997 of the GT24 cDNA overlap the anonymous microsatellite locus D5S478, therefore placing the GT24 gene on chromosome 5p15 near the Cri-du-Chat deletion locus, a syndrome associated with congenital malformation and gross mental retardation. This raises the distinct possibility that mutations or deletions in GT24 have a role in Cri-du-Chat syndrome. The GT24 sequence thus finds use in the diagnosis and therapy of Cri-du-Chat syndrome. On Northern blots, the GT24 gene is expressed as a range of transcripts of 3.9 to 5.0 kb in several regions of adult human brain, but is expressed at only very low levels in most non-neurologic tissues. The open reading frame (ORF) of the GT24 consensus cDNA encodes a protein of 1084 residues with a unique N-terminus, but with homology to proteins with armadillo (arm) repeat motifs at its C-terminus.

Searches of public nucleotide sequence databases also uncovered a murine orthologue of GT24, termed Neural Plakophilin Related Armadillo Protein (NPRAP), a protein of unknown function which contains approximately 147 additional amino acids at the N-terminus (Paffenholz et al., 1997, *Differentiation* 61:293–304). It is unclear whether this difference reflects a true difference between the human and murine orthologues, or an artefact of cloning.

In addition to the GT24 clone (now known as human Neural Plakophilin Related Armadillo Protein (hNPRAP), one further His$^+$, βgal$^+$ yeast-two-hybrid clone (ps11y2h-25) was found to encode another peptide with C-terminal arm repeats. Clone ps11y2h-25 corresponds to a cDNA sequence deposited in GenBank as human protein p0071 (Accession Nos. U81005 and P18824). The ORF of ps11y2h-25/p0071 has 47% overall amino acid sequence identity with hNPRAP, and 70% identity to the arm repeats at residues 390–906 of hNPRAP.

The amino acid sequence alignment of hNPRAP (U81004)(bottom line) and ps11y2h-25/p007 1 (U81005 and P18824)(top line)(solid vertical lines=identity; dotted vertical lines=similarity) is shown in FIG. 1. Since the high GC content of the 5' end sequences (87%) resulted in the recovery only of truncated cDNA clones, residues 1–44 of hNPRAP were derived from genomic DNA sequences. There are 10 putative armadillo repeats in hNPRAP which were identified using the arm consensus sequence (DKNDEKVVTCAAGTLHNLSVHNQNNKMIVRASGG) (SEQ ID NO:3) from PRODOM protein domain entry 138 (Sonnhammer et al., 1994, *Protein Sci.* 3:482–492). These residues also show strong homology to arm repeats in other proteins such as P120cas (Z17804: 32–56% identity, p=1.2× $10^{-133}$), human β-catenin (P35222:28–47% identity, p=2.6× $10^{-4}$), and *D. melanogaster* armadillo (P18824: 26–43% identity, p=1.9×$10^{-4}$).

Examples 2–5 illustrate both the specificity of the PS1:hNPRAP yeast two hybrid interaction and its occurrence under physiological conditions in mammalian cells.

EXAMPLE 2

Reciprocal immunoprecipitation (IP) experiments confirm that PS1 and hNPRAP specifically interact in vitro and that the hNPRAP:PS1 interaction requires the arm repeat of hNPRAP. Also shown is that hNPRAP interacts with PS2.

cDNAs encoding wild type PS1 (wtPS1) holoprotein, and various fragments of hNPRAP tagged at the C-terminus with a myc-tag (EQKLISEEDLN) (SEQ ID NO:4) and/or tagged at the N-terminus with a His-tag, green fluorescent protein (e.g. myc-hNPRAP$_{528-1084}$), or Xpress-epitope tag (Invitrogen) were either transiently expressed (hNPRAP) or stably expressed (PS1) from the pcDNA3 vector (Invitrogen) or from the pEGFP-C1 vector (Clontech, Palo Alto, Calif.) in HEK293 cells. Endogenous β-catenin, α-catenin, γ-catenin, and calnexin were used.

Co-immunoprecipitation and glycerol velocity gradient fractionation were performed as previously described in Yu et al., 1998, *J.Biol.Chem.* 273:16470–16475. Immunoprecipitations were performed on cell lysates 48 hours after transient transfections. Total proteins (2 mg/ml) were extracted from cultured cells or brain tissue using a lysis buffer (0.2% NP-40, 0.5% Triton X-100, 50 mM Tris-HCl [pH7.6], 150 mM NaCl, 2 mM EDTA, 2 mM PMSF, 2 mg/ml each of aprotinin, leupeptin, pepstatin). 1.0 mg proteins were incubated overnight with appropriate antibodies (anti-NPRAP [Y120], anti-PS1 antibody to the), C-terminus or to the TM6-TM7 PS1$_{260-409}$ cytoplasmic loop antibodies 520, 1143, 3027 (Walter et al., 1996, *Molec. Medicine* 2:673–691), to c-myc [9E10.2], β-catenin, α-catenin, γ-catenin (Transduction Laboratories, Lexington, Ky.), calnexin (Stressgen, Vancouver, BC) or pre-immune serum as described in Harlow et al., 1988, Antibodies: A laboratory manual. New York, Cold Spring Harbor Laboratory Press. Protein A Sepharose was subsequently added to the antibody-antigen complex and incubated for 2 hours at 4° C. The beads were washed four times with a washing buffer (0.2% NP-40, 50 mM Tris-HCl[pH7.6], 150 mM NaCl, 2 mM EDTA). IP products were resolved by SDS-PAGE and investigated for the co-immunoprecipitated partners with the corresponding antibody and detection with ECL (Amersham). 5% of the starting detergent lysate (50 mg) was loaded onto the cell extract lane. In experiments using cross-linking, cells were pretreated with 1 mM dithiobis-succinimidyl-proprionate (DSP) for 20 min. on ice.

For glycerol velocity gradient fractionation, brain tissue (1.0 g) was homogenized in a total volume of 5.0 ml of 25 mM Hepes, pH 7.2 at 4° C. with the protease inhibitors described above, and as described in Yu et al., 1998. After spinning at 1000×g for 15 minutes to remove cell debris and nuclei, the resulting supernatant was centrifuged at 100,000×g for 60 minutes to collect cell membranes. The membranes were then washed for 45 minutes with a KCl buffer (1 M KCl, 25 mM Hepes, pH 7.2, and protease inhibitors) and centrifuged again at 100,000×g for 60 min. Cell membranes were then lysed with 1.0% Digitonin in 25 mM Hepes, pH 7.2, 100 mM KCl and protease inhibitors. 0.5 ml of membrane extracts (2 mg/ml) was applied to the top of a 11.5 ml 10–40% (w/v) linear glycerol gradient containing 25 mM Hepes, pH 7.2, 150 mM NaCl, 0.25% Digitonin. Gradients were centrifuged for 15 hours at 35,000 rpm and 4° C. using an SW41 rotor and collected by upward displacement into 1.0 ml fractions using an Isco model 640 density gradient fractionator.

Myc-tagged hNPRAP$_{528-1084}$ was detected in whole lysates of myc-hNPRAP transfected control cells; in IP products from double-transfected HEK293 cells using the anti-PS1 N-terminal antibody 14.3 with prior DSP cross-linking; using anti-PS1$_{260-409}$ loop antibody with cross-linking or without prior cross-linking. No myc-hNPRAP was detected in cells transfected with hNPRAP only and immunoprecipitated with anti-PS1 loop antibody, or in any cell precipitated with pre-immune (PI) serum or with beads but no antibody.

PS1 holoprotein was detected using anti-PS1 N-terminal antibody 14.3 in Western blots of whole lysates from a PS1-transfected control cells and in the anti-myc IP products of a double-transfected cell with no cross-linking.

No PS1 was detected in anti-myc IP products from cells transfected with myc-hNPRAP only, PS1 only, or precipitated with an irrelevant antibody.

PS1 holoprotein and C-terminal PS1 fragments were detected using anti-PS1 N-terminal and anti-loop antibodies (mixed) in Western blots of lysates from HEK293 cells stably expressing PS1 and transiently transfected with hNPRAP cDNA. PS1 holoprotein and C-terminal PS1 but not N-terminal PS1 were co-precipitated with his-tagged hNPRAP (residues 45–1085) on Ni-Agarose columns. An irrelevant his-tagged control protein (His-LacZ) did not co-precipitate any PS1. PS1 alone did not precipitate on the Ni-Agarose column.

Western blots using anti-myc antibody (9E10.2) detected myc-tagged hNPRAP in immunoprecipitates of HEK293 cells stably expressing PS1 and transiently transfected with myc-hNPRAP immunoprecipitation with anti-PS1 loop antibody 1143 and in immunoprecipitates of HEK293 cells stably expressing PS2 and transiently expressing myc-hNPRAP immunoprecipitation with anti-PS2 antibody 972. No myc-tagged hNPRAP was detected in IP products from PS2-only transfected cells or cells immunoprecipitated with pre-immune serum.

In cells expressing PS1 and arm$^+$-hNPRAP, anti-myc antibodies (9E10.2) detected myc-tagged-arm$^+$hNPRAP peptide (GT24 residues 320–1085) in whole lysates and in anti-PS1 immunoprecipitates (anti-PS1 loop antibody 1143), but not in immunoprecipitates using pre-immune serum. The myc-tagged N-terminal arm$^-$-hNPRAP peptide (residues 45–413) was detected in whole lysates of cells doubly transfected with PS1 and arm$^-$-hNPRAP, but not in immunoprecipitates using either anti-PS1 antibodies or pre-immune serum.

This example shows: (1) PS1 and hNPRAP can be reciprocally co-immunoprecipitated from lysates of cells doubly transfected with full-length human PS1 and myc-tagged hNPRAP (myc-hNPRAP$_{528-1084}$). However, co-immunoprecipitation did not occur in single transfected cells or from lysates of cells immunoprecipitated with pre-immune serum, with antibodies to unrelated proteins, or with Protein A Sepharose but no antibody; (2) a non-specific interaction between PS1 and hNPRAP can be excluded because neither protein co-precipitated with other irrelevant cellular proteins such as transfected His-LacZ or with other endoplasmic reticulum proteins such as endogenous calnexin (See Example 5); (3) the co-precipitation requires that the hNPRAP construct contain the C-terminal arm repeats (hNPRAP-arm$^+$). Co-immunoprecipitation does not occur when the hNPRAP transcript encodes only the unique arm N-terminus of hNPRAP. Conversely, the arm-binding domain of PS1 must include residues Thr$_{320}$ to Ala$_{409}$ because: 1) residues 320–409 are the only residues common to all three PS1 yeast two hybrid "bait" constructs; and 2) hNPRAP co-precipitates PS1 holoprotein and PS1-CTF, but does not co-precipitate PS1-NTF. Within the PS1$_{320-409}$ domain, residues 372–399 contain a single arm-motif (20% identity to arm consensus sequence) which is highly conserved in PS2 (91% identity) (Rogaev et al., 1995, *Nature* 376:775–778), and in the invertebrate homologues (82% identity) (Levitan et al. 1995, *Nature* 377:351–354; Boulianne et al., 1997, *NeuroReport* 8:1025–1029).

EXAMPLE 3

To exclude the remote possibility that both the yeast-two-hybrid and the co-immunoprecipitation studies in double transfected cells were artifacts arising from over-expression, both co-immunoprecipitation and glycerol velocity gradient analyses were used to investigate the PS1:NPRAP interaction in vivo in the mammalian central nervous system (CNS). A rabbit polyclonal antibody (Y120) directed to residues 156–170 of human NPRAP (which are predicted to be unique to NPRAP and do not cross react with other arm proteins) was generated. The specificity of this antibody was confirmed by showing that it specifically recognized myc-tagged NPRAP in transiently transfected HEK293 cells, that the Y120 immunoreactive band could be abolished by pre-absorption of the antibody with the cognate peptide, and that the Y120 immununoreactive bands were also detected by an anti-myc monoclonal antibody. Both the anti-myc and the anti-hNPRAP antibodies detected an abundant protein of ~130 kDa (corresponding to full-length myc-tagged NPRAP), and an ~75 kDa species which likely represents a C-terminal proteolytic derivative. The hNPRAP antibody also detected a ~120 kDa species which is not detected by the myc-antibody, and which is likely an N-terminal proteolytic derivative lacking the myc epitope tag. However, both of these lower molecular weight species likely represent aberrantly processed derivatives peculiar to overexpression in HEK293 cells because, in contrast to the full length NPRAP species, they are not detectable in human brain homogenates. To confirm the PS1:NPRAP interaction, anti-hNPRAP antibody was used to investigate anti-PS1 immunoprecipitates from human post-mortem neocortex, and to show that NPRAP is strongly detectable in these anti-PS1 immunoprecipitates. Glycerol velocity gradient analysis of lysates of murine neocortex revealed that NPRAP co-fractionates with the high molecular weight PS1-NTF and PS1-CTF containing complexes (~250 kDa).

EXAMPLE 4

In situ hybridizations in post-natal brain tissue were performed on 18 μm sections from approximately 4 month old murine brain (Moser et al., 1991, *Neuron* 14:509–517). Digoxigenin-labelled antisense or sense strand cRNA probes were generated from the unique sequence at 788–1085 bp of hNPRAP cDNA (Boehinger Mannheim). Sections were hybridized with 100 μL of either antisense or sense probe at a final concentration of 200 ng/ml in 50% formamide, 3×SSC, 0.1% Ficoll, 0.1% polyvinylpyrrolidone, 1% BSA, 500 μg/ml ssDNA, 500 μg/ml tRNA, 10 mM DTT, 10% dextran sulphate at 45° C. overnight in a humidified chamber, and then processed as described by Takeichi et al., 1995, *Curr. Opin. Cell Biol.* 7:619–627. Day E8.5, E10.5, E11.5 and E13.5 embryos ("E"=embryonic post-conception) were fixed in 4% paraformaldehyde, 30–40% sucrose, embedded in OCT and sectioned at 12 μm. Sections were processed as above except for the addition of digestion with 0.01% Proteinase K at 37° C. for 20 min prior to the TEA acetic anhydride step.

In situ hybridization of digoxigenin-labelled anti-sense strand hNPRAP cRNA probes in 4 month post-natal mouse brain showed specific intense staining of neurons in hippocampus, dentate, scattered neocortical, cerebellar Purkinje and granule cells. There was prominent expression in CD1 mouse dorsal root ganglia and neural tube at day E13.5. Sense strand probes produced only minor background signals.

The in situ hybridization studies indicated that the transcriptional pattern of PS1 and NPRAP overlap in the brain of 4 month old mice and in murine embryos. In adult mouse brain both genes are expressed at high levels in dentate and hippocampal neurons, in scattered neocortical neurons, and in cerebellar Purkinje cells in adult mouse brain. (Lee et al., 1996, *J. Neurosci.* 16:7513–7525; Levesque et al., manuscript in prep; Paffenholz et al., 1997, *Differentiation* 61:293–304). Similarly, there is overlap of the embryonic patterns of regional expression of PS1 and NPRAP. Both genes are prominently transcribed for instance in the neural tube and dorsal root ganglia at day E10.5. Confocal laser micrographs of disassociated MDCK cells transiently expressing PS1 (PS1 antibody 14.3, FITC conjugated secondary, green color) and His-tagged-hNPRAP (using GT24 cDNA in pcDNA3.1 vector, Invitrogen) (anti-Express antibody, Rhodamine conjugated secondary, red color) showed colocalization of PS1 and hNPRAP. Experiments using arm$^-$ constructs show diffuse cytoplasmic localization.

In MDCK cells forming intercellular contacts, Green Fluorescent Protein-tagged hNPRAP (pEGFP-C1 vector, Clontech, Palo Alto, Calif.) is predominantly localized near the cell membrane. Experiments using only myc-tagged hNPRAP showed similar results. These immunocytochemical studies in doubly-transfected CHO and MDCK cells revealed that transfected epitope tagged hNPRAP has a variable intracellular distribution. In disassociated cells, hNPRAP has a predominantly perinuclear cytoplasmic distribution contiguous with that of PS1. In contrast, in confluent cells with abundant cell:cell contacts, hNPRAP is predominantly located beneath the cell membrane close to inter-cellular contact zones.

The fact that only PS1 residues 320–409 are contained in all three PS1 yeast two hybrid "bait" constructs, the fact that the smallest hNPRAP "trapped" clone would be predicted to encode only the C-terminal arm repeat (residues 863–1084), and the results of the immunoprecipitation experiments cumulatively support that the PS1:hNPRAP interaction occurs between the C-terminal arm repeats in hNPRAP and residues Thr$_{320}$ to Ala$_{409}$ in PS1. Residues 372–399 of PS1 contain a single arm-motif (20% identity to arm consensus sequence) that is highly conserved not only in PS2 (91% identity) (Rogaev et al., 1995, *Nature* 376:775–778), but also in the invertebrate homologues (82% identity) (Levitan et al., 1995, *Nature* 377:351–354; Boulianne et al., 1997, *NeuroReport* 8:1025–1029). As would be predicted, co-immunoprecipitation experiments in double transfected HEK293 cells reveal that PS2 also interacts with hNPRAP.

EXAMPLE 5

The validity of the PS1:hNPRAP interaction and the hypothesis that it arises from an interaction involving residues 372–399 of PS1 were confirmed by in vitro affinity chromatography experiments.

A His-tagged PS1 loop fragment corresponding to residues 266–409 was covalently linked to an Affi-Gel resin (BioRad) and then incubated with whole lysates of HEK293 cells stably expressing myc-tagged hNPRAP. The resulting complexes were washed repeatedly and the specifically interacting proteins were eluted in 1% SDS and examined by Western blotting using anti-myc antibodies. In vitro affinity chromatography suggests that the PS1:hNPRAP interaction involves the arm-repeat of hNPRAP and residues 372–399 of PS1. myc-tagged arm$^+$-hNPRAP (GT24/arm+) can be detected on Western blots of eluates from the affinity column containing immobilized PS1 cytoplasmic loop residues 266–409. The presence of large quantities of myc-tagged hNPRAP in these eluates clearly demonstrates a high affinity for the PS1 loop. Binding is absent with resin alone, and greatly diminished by pre-incubation with recombinant PS1$_{372-399}$ peptide. myc-tagged arm$^-$-hNPRAP (GT24/arm−) was not detected in the column eluate, but was present in the column flow through. The specificity of this interaction is supported by the following observations. First, myc-hNPRAP does not bind non-specifically to the blocked resin alone. Second, myc-tagged hNPRAP lacking the arm repeats (hNPRAP residues 43–413) does not bind to the immobilized PS1 loop, but appears in the in the column flow-through. Third, other myc-tagged cytoplasmic proteins (e.g. myc-tagged anti-secretory factor) do not bind to the immobilized PS1 loop. Finally, binding of hNPRAP to the immobilized PS1 loop domain can be competitively inhibited by pre-incubation of the hNPRAP-containing cell lysates with a synthetic peptide corresponding to the PS1 arm-like sequence at PS1 residues 372–399. The hNPRAP:PS1 interaction, however, was not affected by pre-incubation with a control peptide corresponding to the TM1-2 loop of PS1 (residues 100–133).

EXAMPLE 6

The results described in Examples 2–5 support the notion that there is a specific interaction between PS1 and hNPRAP. Since, however, the yeast-two-hybrid studies also detected an interaction between PS1 and a closely-related arm protein PS1ly28-25/p0071, a study was conducted to determine whether PS1 might interact promiscuously with several members of the arm-repeat protein family.

Western blots of anti-PS 1 immunoprecipitates from PS1 transfected HEK293 cells were examined for the presence of other arm proteins expressed endogenously in HEK293 cells. Endogenous β-catenin, but not endogenous α-catenin, γ-catenin, or calnexin were detected in Western blots of immunoprecipitation products from HEK293 cells stably transfected with PS1, using either antibodies to PS1 cytoplasmic loop or to the PS1 N-terminus. These studies reveal that the anti-PS1 immunoprecipitates contain endogenous β-catenin but not α-catenin or γ-catenin, and suggest that PS1 selectively interacts only with a subset of armadillo proteins. Endogenous β-catenin was also found to co-precipitate with transfected PS2 following immunopreciptiation of HEK293 cell lysates with anti-PS2 antibodies, but not with pre-immune serum.

EXAMPLE 7

In view of the effect of null mutations on developmental signalling pathways in *C. elegans* and mice (Levitan et al., 1995, *Nature*, 377:351–354; Wong et al., 1997, *Nature* 387:288–292; Shen et al., 1997, *Cell* 89:629–639), the effect of mutations in PS1 and PS2 on the nuclear translocation of endogenous β-catenin following activation of the Wnt/armadillo signal transduction pathway by lithium induced inhibition of glycogen-synthetase-kinase-3β (Stambolic et al., 1996, *Curr. Biol.* 6:1664–1668) was examined to determine whether the PS:arm interactions had a functional role.

Nuclear β-catenin was quantitatively assessed either by immunocytochemistry in native fibroblasts or by Western blotting of nuclear fractions from transfected HEK293 cells. Native fibroblasts obtained by skin biopsy from normal subjects or subjects with PS1 or PS2 mutations were plated at low density. After approximately 65 hours the medium was replaced with media containing 20 mM lithium chloride for 3 hours. The cells were then fixed for 10 min. in 2% paraformaldehyde, incubated with 5% FBS for 30 min., stained with mouse monoclonal anti-β-catenin antibodies (1:500, Transduction Labs) at 4° C. overnight, and counter-stained with Hoechst 33342 dye (Molecular Probes) to label nuclei. β-catenin positive and negative nuclei were then directly counted in approximately 400 cells from different fields.

HEK293 cell lines stably transfected with wild type PS1 (wt2 and sw/wt6), Leu392Val-mutant PS1 (VL25 and VL31), wild type PS2 (sw2-9), Asn141Ile mutant PS2 (sw2-VG1) (kindly provided by Dr. D. Selkoe), and Δ290–319 mutant PS1 were grown in Dulbecco's modified Eagle's medium supplemented with 10% (v/v) fetal bovine serum, and were treated with lithium chloride at 5 mM final concentration for 3 hours (Stambolic et al., 1996, *Curr. Biol.* 6:1664–1668). Nuclei were collected from lithium treated and control cells as previously described in Dignam et al., 1983, *Nucl. Acid Res.* 11:1475–1489). Cells were washed once in ice-cold PBS, resuspended in hypotonic lysis buffer (10 mM Hepes (pH 7.9), 10 mM KCl, 0.1 mM EDTA, 0.5 mM dithiothreitol (DTT), 0.05% Nonidet P-40, 0.5 mM phenylmethylsulfonyl fluoride (PMSF), 10 μg/ml aprotinin, 5 μg/ml leupeptin), and incubated for 30 minutes on ice. The nuclei were pelleted by microcentrifugation at 3,500 rpm for 2 minutes at 4° C., and cytoplasmic fractions were collected from the supernatants. Cytoplasmic soluble β-catenin fractions were incubated with Concavalin A-Sepharose beads (Pharmacia Biotech) as previously described (Miller et al., 1997, *J. Cell Biol.* 139:229–243). Nuclear fractions were extracted by resuspending the nuclei in a high-salt buffer (20 mM Hepes, 400 mM NaCl, 1 mM EDTA, 0.5 mM DTT, 0.5 mM PMSF, 10 μg/ml aprotinin, 5 μg/ml leupeptin) and then incubated with Concavalin A-Sepharose beads to remove contaminating cadherin-bound β-catenin. 5 μg protein of each fraction was separated on 10% SDS-PAGE, and blots were probed with mouse monoclonal antibody against β-catenin (25 ng/ml, Transduction Lab.). Signals were detected by ECL (Amersham) and were quantified from the autoradiographs by the NIH Image software package.

To assess nuclear translocation of NFκB, the same cells were incubated with medium alone or medium supplement with 50 ng/ml of Tumour Necrosis Factor-α (PeproTech Inc.) for 30 minutes, and then processed as above. Nuclear NFκB was quantified on Western blots of nuclear preparations using rabbit polyclonal antibody to p65 subunit (Santa Cruz Biotechnology, Santa Cruz, Calif.).

Endogenous β-catenin in mock treated native human fibroblasts was diffused throughout the cell, or predominantly cytoplasmic. After lithium chloride treatment of wild type fibroblasts, β-catenin is strongly localized in nuclei. In heterozygous PS1 mutant fibroblasts (e.g., Ala260Val PS1, Leu286Val PS1 and Met146Leu) lithium induces very little nuclear translocation. Western blot analyses of nuclear preparations showed progressive accumulation of endogenous β-catenin at 0, 30, and 60 minutes after lithium chloride incubation of HEK293 cells transfected with wild type PS1 (wtPS1) or PS2 (wtPS2) but not mutant PS1 (L392V) or mutant PS2 (N141I).

Treatment of the same cells with TNFα induced increased translocation of NFκB, but there were no differences between non-transfected, wild type or mutant PS1, or mutant PS2.

To investigate β-catenin ubiquitin:proteasome-mediated degradation pathways, HEK293 cells were incubated in medium containing 25 mM ALLN (N-acetyl-Leu-Leu-Norleucinal, Sigma) or ALLN plus 5 mM LiCl for 0, 1, 3, or 6 hours. Cells were harvested, lysates were prepared as previously described in Yu et al., 1998, *J.Biol.Chem.* 273:16470–16475, and 10 mg of protein were subjected to SDS-PAGE and Western blotting followed by immunodetection using ECL and a mouse monoclonal anti-β-catenin antibody (Transduction Labs) as previously described in Aberle et al., 1997, *EMBO J.* 16:3797–3804. Equivalent amounts of ubiquitinated and non-ubiquitinated β-catenin were detected in HEK293 cells expressing wild type or mutant PS1 following treatment with a proteasome inhibitor ALLN alone or ALLN with LiCl.

Cleared lysates of HEK293 cells stably expressing mutant or wild type PS1 were immunoprecipitated with a rabbit polyclonal antibody to the $PS1_{260-409}$ loop (1143), the immunoprecipitates were separated by SDS-PAGE, blotted and probed with monoclonal anti-b-catenin antibodies as described by Yu et al., 1998. Equivalent amounts of endogenous b-catenin were co-immunoprecipitated from HEK293 cells with transfected wild type PS1 or mutant PS1. The transfected HEK293 cells contained equivalent amounts of immunoprecipitable PS1 (wt, Leu392Val or D290–319).

This example shows that mutations in PS1/PS2 modulate the translocation of β-catenin into the nucleus. There were no differences in basal levels of nuclear β-catenin between mutant or wild type native fibroblasts, or between untransfected HEK293 cells and HEK293 cells stably transfected with either wild type or mutant PS1 or PS2 cDNAs. However, upon stimulation of the Wnt/armadillo signal transduction pathway by incubation in medium containing 20 mM lithium chloride for three hours, normal fibroblasts showed pronounced translocation of β-catenin into the nucleus (nuclear βcatenin in 33/41 cells). In contrast, nuclear translocation of β-catenin was significantly reduced in fibroblasts from heterozygous carriers of the Met146Leu (87/349), His163Tyr (176/383), Ala260Val (88/337) and Leu286Val (69/370). Lithium-induced nuclear translocation of b-catenin was also significantly reduced in the PS2 Met239Val mutant fibroblasts (285/456). Nuclear translocation in the group of mutant PS1 fibroblasts was more affected than in mutant PS2 fibroblasts. This observation is in accordance with the reduced clinical penetrance and the later age of disease onset in families with PS2 mutations (mean ~65 years versus ~45 years for PS1 mutations) as described in Bird et al., 1997, *Ann. Neurol.* 40:932–936. Similar results were obtained with the HEK293 cells. Thus, nuclear β-catenin levels substantially increased in HEK293 cells expressing either endogenous PS1/PS2 (6.8) fold), transfected wild type human PS1 (6.9) fold), or wild type PS2 (6.9) fold). In contrast, nuclear β-catenin levels increased only 2.1 fold in HEK293 cells with mutant PS1 (PS1 Leu392Val: 4.4 fold; PS1 Δ290–319: 3.5 fold) and only 1.2 fold in cells expressing mutant PS2 (PS2 Asn141Ile: 1.8 fold). These differences in nuclear β-catenin are not associated with differences in total cellular β-catenin, and cannot be ascribed to differences in PS1 levels, because despite the fact that untransfected HEK293 cells express far lower levels of endogenous PS1, nuclear β-catenin levels were higher in lithium treated untransfected HEK293 cells than in the mutant PS1 transfected HEK293 cells. Finally, in contrast to the changes in nuclear translocation of β-catenin, nuclear translocation of NFκB in response to Tumour Necrosis Factor-α was not affected by PS1 mutations. The latter observation argues that alterations in β-catenin mediated signal transduction mechanisms associated with presenilin mutations does not arise from a non-specific abnormality in nuclear protein transport.

To confirm that the effect of PS1 missense mutations was a specific effect of pathogenic amino acid substitutions and did not occur with non-pathogenic substitutions, these experiments were repeated in fibroblasts from a heterozygous carrier of the PS1 Glu318Gly polymorphism (which is not associated with increased risk for AD or with abnormal bAPP processing—(Mattila et al., 1998, *Ann. Neurol.* in press. Both basal nuclear b-catenin levels (29/489 nuclei) and Li$^+$ induced nuclear translocation (343/451 nuclei) in the PS1 Glu318Gly fibroblasts were indistinguishable from normal control fibroblasts.

Based on these discoveries, Applicants believe that some of the PS1 mutations in the large cytoplasmic loop might directly disrupt the putative PS1:arm interaction domain at residues 372–399. However, quantitative liquid β-galactosidase assays indicate that there is not a large difference between the yeast-two-hybrid interaction of hNPRAP with wild type $PS1_{266-409}$ loop bait sequences compared to its interaction with the mutant Leu286Val $PS1_{266-409}$ bait sequences (βgal activities ±SEM: Wild-type=7.99±0.33; L286V=6.90±0.50 units, p=n.s.). Furthermore, several of the mutations that were tested affect residues remote from the cytoplasmic loop. An alternate explanation revolves around a putative role for the presenilins and homologous proteins such as SPE4 in the docking and trafficking of a subset of cellular proteins such as the major sperm protein in the case of SPE4. In this regard, it may be relevant that another class of armadillo containing proteins, the importins (Gorlich, 1997, *Curr. Opin. Cell Biol.*, 9:412–419), are involved in the facilitation of translocation of proteins across the nuclear membrane (which together with the endoplasmic reticulum is a major intracellular site of presenilin protein expression (De Strooper et al., 1997, *J. Biol. Chem* 272:3590–3598; Walter et al., 1996, *Molec. Medicine* 2:673–691)). Presenilin mutations may cause a dominant gain of aberrant function by causing anomalous and/or misdirected trafficking of a limited number of interacting partners. This would be in agreement with results which suggest that presenilin mutations are associated with mistrafficking of βAPP (Martin et al., 1995, *NeuroReport* 7:217–220; Scheuner et al., 1996, *Nature Med.*, 2:864–870; Citron et al., 1997, *Nature Med.* 3:67–72; Duff et al., 1996, *Nature* 383:710–713; Borchelt et al., 1996, *Neuron*, 17:1005–1013).

Mutations in PS1 and PS2 may cause abnormalities in transcriptional activity in response to receptor mediated signals. Alternatively, by disturbing the intracellular compartmental distribution of arm proteins such as β-catenin, mutations in PS1 or PS2 may disturb their function at inter-cellular junctions. Interactions between catenins (such as β-catenin or APC) and cadherins (such as N-cadherin or cadherin-14) are thought to be important in the maintenance of CNS synapses (Bhat et al., 1994, *J. Neurosci.* 14:3059–3071; Takeichi, 1995, *Curr. Opin. Cell Biol.* 7:619–627; Uchida et al., 1996, *J. Cell Biol.* 135:767–779; Shibata et al., 1997, *J. Biol. Chem.* 272:5236–5240). Synaptic dysmorphism and synaptic loss is a prominent part of the pathology of AD (Masliah et al., 1993, *Brain Path* 3:77–85; Jellinger, 1996, *J. Neural Trans.* 47 (Suppl.):1–29).

Many modifications and variations of this invention can be made without departing from its spirit and scope, as will be apparent to those skilled in the art. The specific embodiments described herein are offered by way of example only, and the invention is to be limited only by the terms of the appended claims, along with the fill scope of equivalents to which such claims are entitled.

All patent and non-patent publications cited in this specification are indicative of the level of skill in the art to which this invention pertains. All these publications and patent applications are herein incorporated by reference to the same extent as if each individual publication or patent application was specifically and individually indicated to be incorporated by reference.

What is claimed is:

1. A method for identifying substances that modulate the nuclear translocation of an armadillo protein, comprising:
   (a) providing a culture of cells that express said armadillo protein and a mutant presenilin 1 (PS1) protein, or a functional fragment thereof, wherein the mutant PS1 protein, or functional fragment thereof binds said armadillo protein, and wherein the mutant PS1 protein comprises at least one mutation relative to a normal PS1 protein, wherein the normal PS1 protein has an amino acid sequence of SEQ ID NO. 1;
   (b) contacting said culture with a test substance;
   (c) inducing nuclear translocation of said armadillo protein in said cells; and
   (d) measuring levels of nuclear armadillo protein as compared to a control as an indication of modulatory activity of said test substance.

2. The method of claim 1, wherein said armadillo protein is β-catenin.

3. The method of claim 1, wherein said armadillo protein is human Neural Plakophilin Related Armadillo Protein.

4. The method of claim 1, wherein said armadillo protein is p0071.

5. The method of claim 1, wherein (c) comprises culturing said cells in the presence of a lithium salt.

6. The method of claim 1, wherein said mutant PS1 protein comprises amino acid residues from about 260 to about 409 of a mutant PS1 protein, wherein the amino acid positions correspond to the wild-type human PS1 sequence defined by SEQ ID NO: 1.

7. The method of claim 1, wherein said mutant PS1 protein comprises amino acid residues from about 372 to about 399 of a mutant PS1 protein, wherein the amino acid positions correspond to the wild-type human PS1 sequence defined by SEQ ID NO: 1.

8. The method of claim 1, wherein said cells are selected from the group consisting of fibroblasts, leukocytes, neuronal cells, human embryonic kidney cells and D. melanogaster cells.

9. A method for identifying substances that modulate the nuclear translocation of an armadillo protein, comprising:
   (a) providing a culture of cells that express said armadillo protein and a mutant presenilin 2 (PS2) protein, or a functional fragment thereof, wherein the mutant PS2 protein, or functional fragment thereof binds said armadillo protein, and wherein the mutant PA2 protein comprises at least one mutation relative to a normal PS2 protein, wherein the normal PS2 protein has an amino acid sequence of SEQ ID NO. 2;
   (b) contacting said culture with a test substance;
   (c) inducing nuclear translocation of said armadillo protein in said cells; and
   (d) measuring levels of nuclear armadillo protein as compared to a control as an indication of modulatory activity of said test substance.

10. The method of claim 9, wherein said armadillo protein is β-catenin.

11. The method of claim 9, wherein said armadillo protein is human Neural Plakophilin Related Armadillo Protein.

12. The method of claim 9, wherein said armadillo protein is p0071.

13. The method of claim 9, wherein (c) comprises culturing said cells in the presence of a lithium salt.

14. The method of claim 9, wherein said mutant PS2 protein comprises amino acid residues from about 266 to about 390 of a mutant PS2 protein, wherein the amino acid positions correspond to the wild-type human PS2 sequence defined by SEQ ID NO: 2.

15. The method of claim 9, wherein said mutant PS2 protein comprises amino acid residues from about 350 to about 380 of a mutant PS2 protein, wherein the amino acid positions correspond to the wild-type human PS2 sequence defined by SEQ ID NO: 2.

16. The method of claim 9, wherein said cells are selected from the group consisting of fibroblasts, leukocytes, neuronal cells, human embryonic kidney cells and D. melanogaster cells.

* * * * *

UNITED STATES PATENT AND TRADEMARK OFFICE
CERTIFICATE OF CORRECTION

PATENT NO. : 6,955,896 B2
DATED : October 18, 2005
INVENTOR(S) : St. George-Hyslop et al.

It is certified that error appears in the above-identified patent and that said Letters Patent is hereby corrected as shown below:

Title page,
Item [73], Assignee, delete "The Governing Council of the Unversity of Toronto, Ontario (CA)" and substitute -- The Governing Council of the University of Toronto, Ontario (CA) --.

Signed and Sealed this

Third Day of January, 2006

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 467
<212> TYPE: PRT
<213> ORGANISM: Homo Sapien

<400> SEQUENCE: 1

Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255
```

-continued

```
Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 2
<211> LENGTH: 448
<212> TYPE: PRT
<213> ORGANISM: Homo Sapien

<400> SEQUENCE: 2

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
```

-continued

```
            145                 150                 155                 160
Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Thr Val
            195                 200                 205

Trp Asn Phe Gly Ala Val Gly Met Val Cys Ile His Trp Lys Gly Pro
            210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
            275                 280                 285

Phe Pro Ala Leu Ile Tyr Ser Ser Ala Met Val Trp Thr Val Gly Met
            290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
            355                 360                 365

Phe Tyr Ser Val Leu Val Gly Lys Ala Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
    435                 440                 445
```

<210> SEQ ID NO 3
<211> LENGTH: 1084
<212> TYPE: PRT
<213> ORGANISM: Homo Sapien
<220> FEATURE:
<221> NAME/KEY: UNSURE
<222> LOCATION: (115)
<223> OTHER INFORMATION: Xaa can be any amino acid

<400> SEQUENCE: 3

```
Met Thr Phe Asn Ala Gly Pro Ser Leu Leu Ser Gln Ser Ala Leu Gln
1               5                   10                  15

Leu Asn Ser Lys Pro Glu Gly Ser Phe Gln Tyr Pro Ala Ser Tyr His
            20                  25                  30

Ser Asn Gln Thr Leu Ala Leu Glu Glu Thr Thr Pro Ser Gln Leu Pro
        35                  40                  45

Ala Arg Gly Thr Gln Ala Arg Ala Thr Gly Gln Ser Phe Ser Gln Gly
    50                  55                  60
```

-continued

```
Thr Thr Ser Arg Ala Gly His Leu Ala Gly Pro Glu Pro Ala Pro Pro
 65                  70                  75                  80

Pro Pro Pro Pro Pro Arg Glu Pro Phe Ala Pro Ser Leu Gly Ser Ala
                 85                  90                  95

Phe His Leu Pro Asp Ala Pro Pro Ala Ala Ala Ala Ala Ala Leu Tyr
            100                 105                 110

Tyr Ser Xaa Ser Thr Leu Pro Ala Pro Pro Arg Gly Gly Ser Pro Leu
            115                 120                 125

Ala Ala Pro Gln Gly Gly Ser Pro Thr Lys Leu Gln Arg Gly Gly Ser
130                 135                 140

Ala Pro Glu Gly Ala Thr Tyr Ala Ala Pro Arg Gly Ser Ser Pro Lys
145                 150                 155                 160

Gln Ser Pro Ser Arg Leu Ala Lys Ser Tyr Ser Thr Ser Ser Pro Ile
                165                 170                 175

Asn Ile Val Val Ser Ser Ala Gly Leu Ser Pro Ile Arg Val Thr Ser
            180                 185                 190

Pro Pro Thr Val Gln Ser Thr Ile Ser Ser Ser Pro Ile His Gln Leu
            195                 200                 205

Ser Ser Thr Ile Gly Thr Tyr Ala Thr Leu Ser Pro Thr Lys Arg Leu
210                 215                 220

Val His Ala Ser Glu Gln Tyr Ser Lys His Ser Gln Glu Leu Tyr Ala
225                 230                 235                 240

Thr Ala Thr Leu Gln Arg Pro Gly Ser Leu Ala Ala Gly Ser Arg Ala
                245                 250                 255

Ser Tyr Ser Ser Gln His Gly His Leu Gly Pro Glu Leu Arg Ala Leu
            260                 265                 270

Gln Ser Pro Glu His His Ile Asp Pro Ile Tyr Glu Asp Arg Val Tyr
            275                 280                 285

Gln Lys Pro Pro Met Arg Ser Leu Ser Gln Ser Gln Gly Asp Pro Leu
290                 295                 300

Pro Pro Ala His Thr Gly Thr Tyr Arg Thr Ser Thr Ala Pro Ser Ser
305                 310                 315                 320

Pro Gly Val Asp Ser Val Pro Leu Gln Arg Thr Gly Ser Gln His Gly
                325                 330                 335

Pro Gln Asn Ala Ala Ala Ala Thr Phe Gln Arg Ala Ser Tyr Ala Ala
            340                 345                 350

Gly Pro Ala Ser Asn Tyr Ala Asp Pro Tyr Arg Gln Leu Gln Tyr Cys
            355                 360                 365

Pro Ser Val Glu Ser Pro Tyr Ser Lys Ser Gly Pro Ala Leu Pro Pro
370                 375                 380

Glu Gly Thr Leu Ala Arg Ser Pro Ser Ile Asp Ser Ile Gln Lys Asp
385                 390                 395                 400

Pro Arg Glu Phe Gly Trp Arg Asp Pro Glu Leu Pro Glu Val Ile Gln
                405                 410                 415

Met Leu Gln His Gln Phe Pro Ser Val Gln Ser Asn Ala Ala Ala Tyr
            420                 425                 430

Leu Gln His Leu Cys Phe Gly Asp Asn Lys Ile Lys Ala Glu Ile Arg
            435                 440                 445

Arg Gln Gly Gly Ile Gln Leu Leu Val Asp Leu Leu Asp His Arg Met
450                 455                 460

Thr Glu Val His Arg Ser Ala Cys Gly Ala Leu Arg Asn Leu Val Tyr
465                 470                 475                 480
```

```
Gly Lys Ala Asn Asp Asn Lys Ile Ala Leu Lys Asn Cys Gly Gly
            485                 490                 495
Ile Pro Ala Leu Val Arg Leu Leu Arg Lys Thr Thr Asp Leu Glu Ile
            500                 505                 510
Arg Glu Leu Val Thr Gly Val Leu Trp Asn Leu Ser Ser Cys Asp Ala
            515                 520                 525
Leu Lys Met Pro Ile Ile Gln Asp Ala Leu Ala Val Leu Thr Asn Ala
            530                 535                 540
Val Ile Ile Pro His Ser Gly Trp Glu Asn Ser Pro Leu Gln Asp Asp
545                 550                 555                 560
Arg Lys Ile Gln Leu His Ser Ser Gln Val Leu Arg Asn Ala Thr Gly
                565                 570                 575
Cys Leu Arg Asn Val Ser Ser Ala Gly Glu Glu Ala Arg Arg Arg Met
                580                 585                 590
Arg Glu Cys Asp Gly Leu Thr Asp Ala Leu Leu Tyr Val Ile Gln Ser
            595                 600                 605
Ala Leu Gly Ser Ser Glu Ile Asp Ser Lys Thr Val Glu Asn Cys Val
            610                 615                 620
Cys Ile Leu Arg Asn Leu Ser Tyr Arg Leu Ala Ala Glu Thr Ser Gln
625                 630                 635                 640
Gly Gln His Met Gly Thr Asp Glu Leu Asp Gly Leu Leu Cys Gly Glu
                645                 650                 655
Ala Asn Gly Lys Asp Ala Glu Ser Ser Gly Cys Trp Gly Lys Lys Lys
                660                 665                 670
Lys Lys Lys Lys Ser Gln Asp Gln Trp Asp Gly Val Gly Pro Leu Pro
            675                 680                 685
Asp Cys Ala Glu Pro Pro Lys Gly Ile Gln Met Leu Trp His Pro Ser
            690                 695                 700
Ile Val Lys Pro Tyr Leu Thr Leu Leu Ser Glu Cys Ser Asn Pro Asp
705                 710                 715                 720
Thr Leu Glu Gly Ala Ala Gly Ala Leu Gln Asn Leu Ala Ala Gly Ser
                725                 730                 735
Trp Lys Trp Ser Val Tyr Ile Arg Ala Ala Val Arg Lys Glu Lys Gly
                740                 745                 750
Leu Pro Ile Leu Val Glu Leu Leu Arg Ile Asp Asn Asp Arg Val Val
            755                 760                 765
Cys Ala Val Ala Thr Ala Leu Arg Asn Met Ala Leu Asp Val Arg Asn
770                 775                 780
Lys Glu Leu Ile Gly Lys Tyr Ala Met Arg Asp Leu Val His Arg Leu
785                 790                 795                 800
Pro Gly Gly Asn Asn Ser Asn Asn Thr Ala Ser Lys Ala Met Ser Asp
                805                 810                 815
Asp Thr Val Thr Ala Val Cys Cys Thr Leu His Glu Val Ile Thr Lys
            820                 825                 830
Asn Met Glu Asn Ala Lys Ala Leu Arg Asp Ala Gly Gly Ile Glu Lys
                835                 840                 845
Leu Val Gly Ile Ser Lys Ser Lys Gly Asp Lys His Ser Pro Lys Val
            850                 855                 860
Val Lys Ala Ala Ser Gln Val Leu Asn Ser Met Trp Gln Tyr Arg Asp
865                 870                 875                 880
Leu Arg Ser Leu Tyr Lys Lys Asp Gly Trp Ser Gln Tyr His Phe Val
                885                 890                 895
Ala Ser Ser Ser Thr Ile Glu Arg Asp Arg Gln Arg Pro Tyr Ser Ser
```

```
                    900                 905                 910
Ser Arg Thr Pro Ser Ile Ser Pro Val Arg Val Ser Pro Asn Asn Arg
        915                 920                 925

Ser Ala Ser Ala Pro Ala Ser Pro Arg Glu Met Ile Ser Leu Lys Glu
        930                 935                 940

Arg Lys Thr Asp Tyr Glu Cys Thr Gly Ser Asn Ala Thr Tyr His Gly
945                 950                 955                 960

Gly Lys Gly Glu His Thr Ser Arg Lys Asp Ala Met Thr Ala Gln Asn
                965                 970                 975

Thr Gly Ile Ser Thr Leu Tyr Arg Asn Ser Tyr Gly Ala Pro Ala Glu
                980                 985                 990

Asp Ile Lys His Asn Gln Val Ser Ala Gln Pro Val Pro Gln Glu Pro
                995                 1000                1005

Ser Arg Lys Asp Tyr Glu Thr Tyr Gln Pro Phe Gln Asn Ser Thr Arg
        1010                1015                1020

Asn Tyr Asp Glu Ser Phe Phe Glu Asp Gln Val His His Arg Pro  Pro
1025                1030                1035                1040

Ala Ser Glu Tyr Thr Met His Leu Gly Leu Lys Ser Thr Gly Asn Tyr
                1045                1050                1055

Val Asp Phe Tyr Ser Ala Ala Arg Pro Tyr Ser Glu Leu Asn Tyr Glu
                1060                1065                1070

Thr Ser His Tyr Pro Ala Ser Pro Asp Ser Trp Val
                1075                1080

<210> SEQ ID NO 4
<211> LENGTH: 1193
<212> TYPE: PRT
<213> ORGANISM: Homo Sapien

<400> SEQUENCE: 4

Met Pro Ala Pro Glu Gln Ala Ser Leu Val Glu Glu Gly Gln Pro Gln
1               5                   10                  15

Thr Arg Gln Glu Ala Ala Ser Thr Gly Pro Cys Met Glu Pro Glu Thr
            20                  25                  30

Thr Ala Thr Thr Ile Leu Ala Ser Val Lys Glu Gln Glu Leu Gln Phe
        35                  40                  45

Gln Arg Leu Thr Arg Glu Leu Glu Val Glu Arg Gln Ile Val Ala Ser
    50                  55                  60

Gln Leu Glu Arg Cys Arg Leu Gly Ala Glu Ser Pro Ser Ile Ala Ser
65                  70                  75                  80

Thr Ser Ser Thr Glu Lys Ser Phe Pro Trp Arg Ser Thr Asp Val Pro
                85                  90                  95

Asn Thr Gly Val Ser Lys Pro Arg Val Ser Asp Ala Val Gln Pro Asn
                100                 105                 110

Asn Tyr Leu Ile Arg Thr Glu Pro Glu Gln Gly Thr Leu Tyr Ser Pro
            115                 120                 125

Glu Gln Thr Ser Leu His Glu Ser Glu Gly Ser Leu Gly Asn Ser Arg
        130                 135                 140

Ser Ser Thr Gln Met Asn Ser Tyr Ser Asp Ser Gly Tyr Gln Glu Ala
145                 150                 155                 160

Cys Ser Phe His Asn Ser Gln Asn Val Ser Lys Ala Asp Asn Arg Gln
                165                 170                 175

Gln His Ser Phe Ile Gly Ser Thr Asn Asn His Val Val Arg Asn Ser
                180                 185                 190
```

-continued

Arg Ala Glu Gly Gln Thr Leu Val Gln Pro Ser Val Ala Asn Arg Ala
        195                 200                 205

Met Arg Arg Val Ser Ser Val Pro Ser Arg Ala Gln Ser Pro Ser Tyr
    210                 215                 220

Val Ile Ser Thr Gly Val Ser Pro Ser Arg Gly Ser Leu Arg Thr Ser
225                 230                 235                 240

Leu Gly Ser Gly Phe Gly Ser Pro Ser Val Thr Asp Pro Arg Pro Leu
                245                 250                 255

Asn Pro Ser Ala Tyr Ser Ser Thr Leu Pro Ala Ala Arg Ala Ala
            260                 265                 270

Ser Pro Tyr Arg Ser Gln Arg Pro Ala Ser Pro Thr Ala Ile Arg Arg
        275                 280                 285

Ile Gly Ser Val Thr Ser Arg Gln Thr Ser Asn Pro Asn Gly Pro Thr
    290                 295                 300

Pro Gln Tyr Gln Thr Thr Ala Arg Val Gly Ser Pro Leu Thr Leu Thr
305                 310                 315                 320

Asp Ala Gln Thr Arg Val Ala Ser Pro Ser Gln Gly Gln Val Cys Ser
                325                 330                 335

Ser Ser Pro Lys Arg Ser Gly Met Thr Ala Val Pro Gln His Leu Gly
            340                 345                 350

Pro Ser Leu Gln Arg Thr Val His Asp Met Glu Gln Phe Cys Gln Gln
        355                 360                 365

Gln Tyr Asp Ile Tyr Glu Arg Met Val Pro Pro Arg Pro Asp Ser Leu
    370                 375                 380

Thr Cys Leu Arg Ser Ser Tyr Ala Ser Gln His Ser Gln Leu Gly Gln
385                 390                 395                 400

Asp Ile Arg Ser Ala Val Ser Pro Asp Leu His Ile Thr Pro Ile Tyr
                405                 410                 415

Glu Cys Arg Thr Tyr Tyr Tyr Ser Pro Val Tyr Arg Ser Pro Asn His
            420                 425                 430

Cys Ile Val Glu Leu Gln Gly Ser Gln Thr Ala Leu Tyr Arg Thr Cys
        435                 440                 445

Val Glu Gly Ile Gly Asn Leu Gln Arg Thr Ser Ser Gln Arg Ser Thr
    450                 455                 460

Leu Thr Tyr Gln Arg Asn Asn Tyr Ala Leu Asn Thr Thr Ala Thr Tyr
465                 470                 475                 480

Ala Glu Pro Tyr Arg Pro Ile Gln Tyr Arg Val Gln Glu Cys Asn Tyr
                485                 490                 495

Asn Arg Leu Gln His Ala Val Pro Ala Asp Asp Gly Thr Thr Arg Ser
            500                 505                 510

Pro Ser Ile Asp Ser Ile Gln Lys Asp Pro Arg Glu Phe Ala Trp Arg
        515                 520                 525

Asp Pro Glu Leu Pro Glu Val Ile His Met Leu Glu His Gln Phe Phe
    530                 535                 540

Ser Val Gln Ala Asn Ala Ala Tyr Leu Gln His Ile Cys Phe Gly
545                 550                 555                 560

Asp Asn Lys Val Lys Met Glu Val Cys Arg Leu Cys Gly Ile Lys His
                565                 570                 575

Leu Val Asp Leu Leu Asp His Arg Val Leu Glu Val Gln Lys Asn Ala
            580                 585                 590

Cys Gly Ala Leu Arg Asn Leu Val Phe Gly Lys Ser Thr Asp Glu Asn
        595                 600                 605

Lys Ile Ala Met Lys Asn Val Gly Gly Ile Phe Ala Leu Leu Arg Ile

-continued

```
            610                 615                 620
Ile Arg Lys Ser Ile Asp Ala Glu Val Arg Glu Ile Val Thr Gly Val
625                 630                 635                 640

Leu Trp Asn Leu Ser Ser Cys Asp Ala Val Lys Met Thr Ile Ile Arg
                645                 650                 655

Asp Ala Leu Ser Thr Leu Thr Asn Thr Val Ile Val Pro His Ser Cys
                660                 665                 670

Trp Asn Asn Ser Ser Phe Asp Asp His Lys Ile Lys Phe Gln Thr
                675                 680                 685

Ser Leu Val Leu Arg Asn Thr Thr Gly Cys Leu Arg Asn Leu Thr Ser
                690                 695                 700

Ala Gly Glu Phe Ala Arg Lys Gln Met Arg Ser Cys Glu Gly Leu Val
705                 710                 715                 720

Asp Ser Leu Leu Tyr Val Ile His Thr Cys Val Asn Thr Ser Asp Tyr
                725                 730                 735

Asp Ser Lys Thr Val Glu Asn Cys Val Cys Thr Leu Arg Asn Leu Ser
                740                 745                 750

Tyr Arg Leu Glu Leu Glu Val Pro Gln Ala Arg Leu Leu Gly Leu Asn
                755                 760                 765

Glu Leu Asp Asp Leu Leu Gly Lys Glu Ser Pro Ser Lys Asp Ser Glu
770                 775                 780

Pro Ser Cys Trp Gly Lys Lys Lys Lys Lys Arg Thr Pro Gln
785                 790                 795                 800

Pro Gln Glu Asp Gln Trp Asp Cys Val Gly Pro Ile Pro Gly Leu Ser
                805                 810                 815

Lys Ser Pro Lys Gly Val Glu Met Leu Trp His Pro Ser Val Val Lys
                820                 825                 830

Pro Tyr Leu Thr Leu Leu Ala Glu Ser Ser Asn Pro Ala Thr Leu Glu
                835                 840                 845

Cys Ser Ala Cys Ser Leu Gln Asn Leu Ser Ala Ser Asn Trp Lys Phe
850                 855                 860

Ala Ala Tyr Ile Arg Gly Gly Arg Pro Lys Arg Lys Cys Leu Pro Ile
865                 870                 875                 880

Leu Val Glu Leu Leu Arg Met Asp Asn Asp Arg Val Val Ser Ser Cys
                885                 890                 895

Ala Thr Ala Leu Arg Asn Met Ala Leu Asp Val Asn Lys Glu Leu Ile
                900                 905                 910

Cys Lys Tyr Ala Met Arg Asp Leu Val Asn Arg Leu Pro Cys Cys Asn
                915                 920                 925

Gly Pro Ser Val Leu Ser Asp Glu Thr Met Ala Ala Ile Cys Cys Ala
930                 935                 940

Leu His Glu Val Thr Ser Lys Asn Met Glu Asn Ala Lys Ala Leu Ala
945                 950                 955                 960

Asp Ser Gly Gly Ile Glu Lys Leu Val Asn Ile Thr Lys Gly Arg Gly
                965                 970                 975

Asp Arg Ser Ser Leu Lys Val Val Lys Ala Ala Ala Gln Val Leu Asn
                980                 985                 990

Thr Leu Trp Gln Tyr Arg Asp Leu Arg Ser Ile Tyr Lys Lys Asp Gly
                995                 1000                1005

Trp Asn His Pro Ile Thr Pro Val Ser Thr Leu Glu Arg Asp Arg Phe
                1010                1015                1020

Lys Ser His Pro Ser Leu Ser Thr Thr Asn Gln Gln Met Ser Pro Ile
1025                1030                1035                1040
```

```
Ile Gln Ser Val Gly Ser Thr Ser Ser Ser Pro Ala Leu Leu Gly Ile
                1045                1050                1055

Arg Asp Pro Arg Ser Glu Tyr Asp Arg Thr Gln Pro Pro Met Gln Tyr
            1060                1065                1070

Tyr Asn Ser Gln Gly Asp Ala Thr His Lys Gly Leu Tyr Pro Gly Ser
        1075                1080                1085

Ser Lys Pro Ser Pro Ile Tyr Ile Ser Ser Tyr Ser Ser Pro Ala Arg
    1090                1095                1100

Glu Gln Asn Arg Arg Leu Gln His Gln Gln Leu Tyr Tyr Ser Gln  Asp
1105                1110            1115                1120

Asp Ser Asn Arg Lys Asn Phe Asp Ala Tyr Arg Leu Tyr Leu Gln Ser
                1125            1130                1135

Pro His Ser Tyr Glu Asp Pro Tyr Phe Asp Asp Arg Val His Phe Pro
            1140                1145                1150

Ala Ser Thr Asp Tyr Ser Thr Gln Tyr Gly Leu Lys Ser Thr Thr Asn
            1155            1160                1165

Tyr Val Asp Phe Tyr Ser Thr Lys Arg Pro Ser Tyr Arg Ala Glu Gln
    1170            1175                1180

Tyr Pro Gly Ser Pro Asp Ser Trp Val
1185                1190
```